US011707881B2

(12) United States Patent
Guillemot

(10) Patent No.: US 11,707,881 B2
(45) Date of Patent: Jul. 25, 2023

(54) DEVICE FOR LASER PRINTING BIOLOGICAL COMPONENTS

(71) Applicants: UNIVERSITÉ DE BORDEAUX, Bordeaux (FR); INSTITUT NATIONAL DE LA SANTE ET DE LA RECHERCHE MEDICALE—INSERM, Paris (FR)

(72) Inventor: Fabien Guillemot, Preignac (FR)

(73) Assignees: Universite de Bordeaux, Bordeaux (FR); Institut National de la Sante et de la Recherche Medicale-Inserm, Paris (FR)

( * ) Notice: Subject to any disclaimer, the term of this patent is extended or adjusted under 35 U.S.C. 154(b) by 183 days.

(21) Appl. No.: 17/229,058

(22) Filed: Apr. 13, 2021

(65) Prior Publication Data

US 2021/0229342 A1    Jul. 29, 2021

Related U.S. Application Data

(62) Division of application No. 15/536,564, filed as application No. PCT/FR2015/053570 on Dec. 17, 2015, now Pat. No. 11,045,996.

(30) Foreign Application Priority Data

Dec. 17, 2014    (FR) ...................................... 1462570

(51) Int. Cl.
*B29C 64/112*    (2017.01)
*C12N 5/00*    (2006.01)
(Continued)

(52) U.S. Cl.
CPC .......... *B29C 64/112* (2017.08); *B29C 64/209* (2017.08); *B29C 64/273* (2017.08);
(Continued)

(58) Field of Classification Search
None
See application file for complete search history.

(56) References Cited

U.S. PATENT DOCUMENTS 5,021,808 A    6/1991    Kohyama
5,521,140 A    5/1996    Matsuda et al.
(Continued)

FOREIGN PATENT DOCUMENTS

JP    S62191157 A    8/1987
JP    2013-179916 A    9/2013
(Continued)

OTHER PUBLICATIONS

Machine translation of JP2013179916A, Sep. 12, 2013 (Year: 2013).*

(Continued)

*Primary Examiner* — Benjamin A Schiffman
(74) *Attorney, Agent, or Firm* — Harness Dickey & Pierce, PLC

(57) ABSTRACT

A method for printing uses at least one bio-ink. The method also uses at least one laser print head to deposit at least one droplet of at least one bio-ink onto a depositing surface of a receiving substrate. The printing method uses at least one nozzle print head to deposit at least one droplet of at least one bio-ink onto a depositing surface of the same receiving substrate as the laser print head.

20 Claims, 5 Drawing Sheets

(51) Int. Cl.
    *C12M 3/00*     (2006.01)
    *C12M 1/00*     (2006.01)
    *B33Y 80/00*     (2015.01)
    *B33Y 10/00*     (2015.01)
    *B41J 2/14*     (2006.01)
    *B33Y 30/00*     (2015.01)
    *B29C 64/209*     (2017.01)
    *B29C 64/273*     (2017.01)
    *C12N 5/077*     (2010.01)
    *C12M 1/26*     (2006.01)

(52) U.S. Cl.
    CPC ............... *B33Y 10/00* (2014.12); *B33Y 30/00* (2014.12); *B33Y 80/00* (2014.12); *B41J 2/14104* (2013.01); *C12M 21/08* (2013.01); *C12M 23/50* (2013.01); *C12N 5/0068* (2013.01); *C12N 5/0654* (2013.01); *B29K 2995/0056* (2013.01); *C12M 33/00* (2013.01); *C12N 2533/90* (2013.01)

(56) References Cited

U.S. PATENT DOCUMENTS

| | | |
|---|---|---|
| 8,240,805 B2 | 8/2012 | Sarger et al. |
| 9,347,037 B2 | 5/2016 | Masutani et al. |
| 9,968,437 B2 | 5/2018 | Tran |
| 10,112,388 B2 * | 10/2018 | Guillemot .......... B41M 5/38207 |
| 2008/0117255 A1 | 5/2008 | Cannon et al. |
| 2013/0017564 A1 | 1/2013 | Guillemot et al. |
| 2015/0246072 A1 | 9/2015 | Bhatia et al. |
| 2015/0351896 A1 | 12/2015 | D'Lima et al. |
| 2016/0288414 A1 | 10/2016 | Ozbolat et al. |
| 2019/0064774 A1 | 2/2019 | Nielsen et al. |
| 2019/0275205 A1 | 9/2019 | D'Lima et al. |
| 2019/0375163 A1 | 12/2019 | Stern et al. |
| 2021/0394444 A1 * | 12/2021 | Guillemot .............. C12M 33/00 |

FOREIGN PATENT DOCUMENTS

| | | |
|---|---|---|
| WO | WO-2003/056320 A2 | 7/2003 |
| WO | WO-2011/107599 A1 | 9/2011 |
| WO | WO-2014/110590 A1 | 7/2014 |
| WO | WO-2016/097619 | 6/2016 |

OTHER PUBLICATIONS

Ovsianikov, et al., "Laser Printing of Cells Into 3D Scaffolds", Biofabrication, vol. 2, No. 1, Mar. 10, 2010.

Saunders et al., "Delivery of Human Fibroblast Cells By Piezoelectric Drop-on-Demand Inkjet Printing", Biomaterials, vol. 29, No. 2, pp. 193-203, Oct. 23, 2007.

* cited by examiner

DEVICE FOR LASER PRINTING BIOLOGICAL COMPONENTS

CROSS-REFERENCE TO RELATED APPLICATIONS

This application is a division of U.S. patent application Ser. No. 15/536,564, filed on Jun. 15, 2017, which is a National Phase Entry of International Patent Application No. PCT/FR2015/053570, filed on Dec. 17, 2015, which claims priority to French Patent Application Serial No. 14/62570, filed on Dec. 17, 2014, all of which are incorporated by reference herein.

BACKGROUND AND SUMMARY

The present invention relates to a method for laser printing biological components and to a device for the implementation thereof. The invention also relates to a method for producing a biological tissue using this printing method.

According to a first procedure, cells can be grown in vitro on a biodegradable macroporous matrix (or scaffold) for obtaining a biological tissue. This first procedure is not fully satisfactory because the growth of the biological tissue can be limited in the depth of the macroporous matrix due to a lack of cell colonization. Besides, this procedure makes it difficult to deal with the complexity of the tissues (which is characterized by a multiplicity of cell types organized in specific and generally anisotropic arrangements).

To overcome these drawbacks, methods for printing biological components have been developed to produce a biological tissue in an automatable manner. According to various documents of the literature, such printing methods are called bio-printing, micro-printing of biological components or simply bio-printing. According to these methods, the biological tissue is obtained by printing droplets of bio-inks. In order to reach some volume, the droplets are arranged in layers which are stacked on each other.

In a first alternative embodiment, the bio-ink is stored in a tank and goes through nozzles or capillaries in order to form droplets that are transferred onto a substrate. This first alternative solution, so-called a nozzle printing includes bio-extrusion, ink-jet printing or micro-valves printing.

Bio-extrusion makes it possible to obtain a significant cell density of the order of 100 million cells per milliliter and a resolution of one millimeter. Micro-valves printing makes it possible to obtain a lesser cell density of the order of several million cells per milliliter and a better resolution of the order of 100 µm. Ink-jet printing makes it possible to obtain a cell density identical with that of micro-valves printing, of less than 10 million cells per milliliter and a better resolution of the order of 10 µm.

In the case of bio-extrusion, the cells are deposited from a first nozzle and a hydrogel is simultaneously deposited from a second nozzle. As an alternative solution, the cells and the hydrogel are mixed in a tank prior to the extrusion. In the two other cases, ink is an aqueous medium containing the cells. According to the alternative solutions, bio-extrusion makes it possible to deposit the ink continuously as filaments or discontinuously as droplets.

According to such nozzle printing modes, as the printing resolution is linked in particular to the nozzle section, only bio-inks with given rheological characteristics can be used for high resolutions. Bio-inks with high cell density can thus be printed with difficulty, with a high resolution since such printing technique induces, upon the passage of ink through the nozzle, high shear stresses liable to damage the cells. Besides, with this type of ink, the risk of nozzles being blocked by the cells is important mainly because of the settling of cells inside the tanks.

A method for printing biological components by laser has been developed in order to be able to use a wide range of bio-inks and achieve high resolution. This printing method, called laser bio-printing, is also known as "Laser-Assisted Bio-printing" (LAB). The invention specifically relates to this type of printing methods. For comparison, bio-laser printing makes it possible to print inks with a high cell density of the order of 100 million cells per milliliter with a resolution of 10 µm.

As illustrated in FIG. 1, a device for laser printing biological components which is based on the so-called "Laser-Induced Forward Transfer" (LIFT) technique, comprises a pulsed laser source 10 emitting a laser beam 12, a system 14 for focusing and orienting the laser beam 12, a donor substrate 16 which comprises at least one bio-ink 18 and a receiving substrate 20 so positioned as to receive droplets 22 emitted from the donor substrate 16. According to this printing technique, the laser beam is pulsed and a droplet is generated on each pulse.

Bio-ink 18 comprises a matrix, for example an aqueous medium, wherein elements are present, for example, cells, to be deposited onto the receiving substrate 20. The donor substrate 16 comprises a blade 24 transparent to the wavelength of the laser beam 12 which is coated with an absorbent layer 26 whereon bio-ink 18 is affixed as a film. The absorbent layer 26 makes it possible to convert light energy into kinetic energy. The laser beam 12 thus produces a punctual heating at the absorbent layer 26 that generates, by vaporization, a gas bubble 28 which, by expansion, causes the ejection of a droplet 30 of bio-ink.

According to a known arrangement, the laser beam 12 impacts the donor substrate 16 by being oriented in an approximately vertical direction and in an upward direction, or in the same direction as the gravitational force G. Bio-ink 18 is thus placed under the blade 24 so as to be oriented downwards, towards the receiving substrate 20 which is placed under the donor substrate 16. Given this arrangement, bio-ink 18 is in the form of a film with a thickness E lower than a given threshold to be held on the blade. This threshold varies in particular according to the surface tension, viscosity and density of bio-ink.

The formation of droplets 30 from the ink film depends on many parameters which relate in particular to the laser beam 12 (wavelength, energy, pulse duration, . . . ), the nature of the bio-ink 18 (surface tension, viscosity, . . . ), to external conditions (temperature, humidity, . . . ). Even though laser printing theoretically makes it possible to reach a high printing rate, insofar as it is possible to generate several tens of thousands of droplets per second, the production of biological tissues is not fast since these droplets represent a few tens of picoliters only. Besides, the donor substrates have to be frequently replaced because they each contain a small volume of ink to be printed of the order of several tens of microliters, only.

According to a second embodiment illustrated in FIG. 2, and disclosed in a publication entitled "Microdroplet deposition through a film-free laser forward technique" published on Oct. 1, 2011 on the site www.elsevier.com, a laser printing device comprises a laser source 32 emitting a laser beam 34, a system 36 for focusing and orienting the laser beam 34, a donor substrate 38 which comprises at least one bio-ink 40 and a receiving substrate 42 so positioned as to receive droplets 44 emitted from the donor substrate 38.

According to the first embodiment, the donor substrate 38 includes no absorbent layer different from the bio-ink. According to this embodiment, the donor substrate 38 includes a tank 46 with no upper wall so that the free surface 48 of the bio-ink 40 contained in the tank faces the receiving substrate 42. To obtain a regular, substantially planar, free surface 48, bio-ink is not a thin film but a volume having a depth of the order of 3 mm. Thus, the tank bottom has no influence on the shape of the free surface 48 of the bio-ink and the side walls of the tank have a limited effect at the periphery of the free surface 48 because of the surface tension.

Given the depth of the volume of bio-ink, the free surface 48 is necessarily directed upwards to stay in the tank and the receiving substrate 42 is positioned above the bio-ink 40. According to this document, to obtain the ejection of a droplet, the laser beam 34 is focused just below the free surface 48 and has a depth of the order of 40 to 80 µm. Thus, the droplets emitted from the free surface 48 are projected toward the receiving substrate 42 in a direction of movement opposite the direction of gravitational force G.

Even though this second embodiment uses donor substrates containing a larger volume of bio-ink, it is not necessarily suitable for bio-inks. As a matter of fact, as indicated above, such bio-inks contain elements to be printed, such as, for instance cells, embedded in a matrix, which tend to settle down on the tank bottom. As the concentration in elements to be printed is low near the free surface, the printed droplets have de facto low concentrations of cells, which is generally detrimental to the printed biological tissue. Besides, according to this method, the number of cells and the concentration of deposited cells can hardly be controlled.

The present invention also aims to solve the drawbacks of the prior art. To this end, the invention relates to a method for printing at least one bio-ink, with said method using at least one laser-type print head to deposit at least one droplet of at least one bio-ink onto a depositing surface of a receiving substrate. The printing method is characterized in that it uses at least one nozzle print head to deposit at least one droplet of at least one bio-ink onto a depositing surface of the same receiving substrate as the print head of the laser type.

This combination makes it possible to increase the production rate of the biological tissues and to obtain more complex biological tissues. For the production of a biological tissue comprising at the same time cells and an extracellular matrix, the materials the extracellular matrix is made of are deposited by the nozzle print head(s) and the cells are deposited by the print head(s) of the laser type.

The invention also relates to a method for making a biological tissue which is characterized in that it comprises the steps consisting in:

Generating a three-dimensional digital representation of the biological tissue to be produced, with said representation comprising several colored or textured volume regions, with each color or texture being associated with a bio-ink, Slicing the representation into a succession of stacked layers, with each layer comprising colored or textured regions which correspond to the volume regions of the representation, For each layer, determining the position of the droplets to be printed of each bio-ink according to the colored or textured regions and the expected volume of each droplet, Printing the different droplets.

The layers preferably have a thickness depending on the size of the droplets. The representation advantageously comprises a plurality of small elementary volume which have different colors or textures depending on the volume region which they belong to.

According to one embodiment, for determining the position of each droplet, each region is filled with identical ellipses which have dimensions depending on the dimensions of the droplets of the bio-ink to be printed in said area, with the center of each ellipse corresponding to the position of the center of a droplet. The ellipses are preferably positioned area by area, in the descending order of sizes.

The invention also relates to a printing device which comprises at least one receiving substrate with a depositing surface and at least one laser-type print head and which is characterized in that it comprises at least one nozzle print head to print at least one bio-ink onto the same receiving substrate as the print head(s) of the laser type. According to another characteristic, the printing device comprises a chamber so configured as to store at least a base supporting a donor substrate, with said chamber being equipped with containment means making it possible to maintain inside an atmosphere adapted to bio-inks.

The chamber preferably has dimensions adapted to store several bases. In this case, the printing device comprises at least one base plate so configured as to be stored inside said chamber, with said base plate comprising a recess for each base. The chamber advantageously includes, on a first side facing the print heads, a first opening enabling the bases to come out and, on another side, a second opening for introducing the bases.

In addition to the chamber, the printing device includes a mobile clamp to move the bases between the chamber and the print head of the laser type. According to another characteristic, the printing device comprises a mobile chassis supporting at least one receiving substrate, a system for guiding and displacing the mobile chassis relative to a chassis in three directions and a control system for controlling the movements of the mobile chassis, with said guide and displacement system and said control system having a micrometric precision.

BRIEF DESCRIPTION OF THE DRAWINGS

Other characteristics and advantages will appear from the following description of the invention, and such description is given by way of example only, with reference to the appended drawings in which.

DETAILED DESCRIPTION

Figure 3:
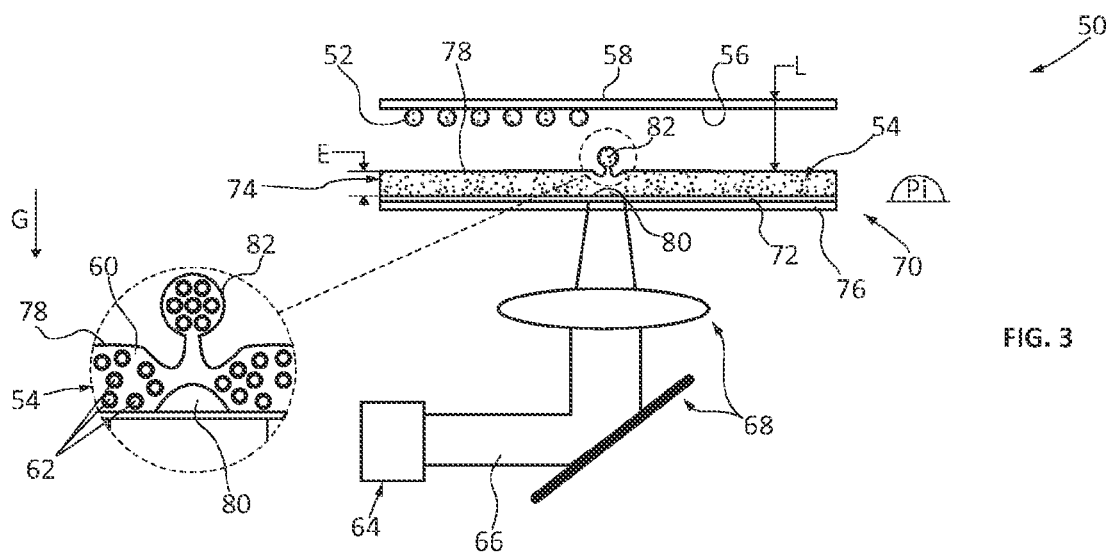
FIG. 3 is a schematic representation of a laser printing device which illustrates the invention.

FIG. 3 shows a printing device 50 for producing at least one biological tissue through a layer by layer assembling according to a predefined arrangement, various components such as an extracellular matrix and various morphogens. Thus, the printing device 50 makes it possible to deposit, layer by layer, droplets 52 of at least one bio-ink 54 onto a depositing surface 56 which corresponds to the surface of a receiving substrate 58 for the first layer or for the last layer deposited on said receiving substrate 58 for the following layers. In order to simplify the representation, the depositing surface 56 corresponds to the surface of the receiving substrate 58 in FIG. 3.

Figure 6:
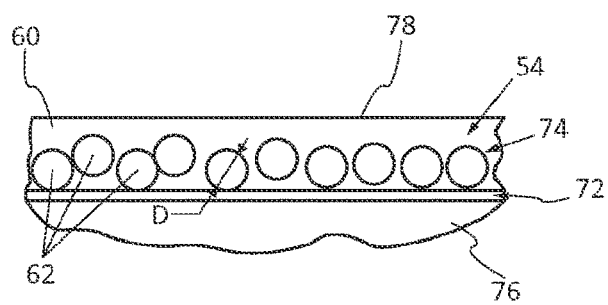
FIG. 6 is a section of a donor substrate illustrating the relationship between the size of the elements to be printed and the thickness of a bio-ink film.

According to one embodiment in FIG. 6, the bio-ink 54 comprises a matrix 60, for example an aqueous medium, wherein elements 62, for example, cells or cell aggregates, to be printed onto the depositing surface 56 can be found. As the case may be, a bio-ink 54 comprises, in the matrix 60, only one kind of elements to be printed 62 or several kinds of elements to be printed 62. In an alternative solution, the bio-ink 54 may comprise one component only.

Bio-ink means, for the present patent application, a biological material or bio-material. For example, the bio-ink only comprises an extracellular matrix (for instance collagen), an extracellular matrix and elements such as cells or cell aggregates, an aqueous medium containing elements such as cells or cell aggregates. The bio-ink 54 is not further described because it can have different types and different rheological characteristics from one ink to another.

This printing device comprises a laser source 64 so configured as to emit a laser beam 66 which is characterized specifically by its wavelength, its frequency, its energy, its diameter, its pulse duration. Preferably, the laser source 64 can be so configured as to adjust at least one characteristic of the laser beam, in particular the energy thereof.

In order to form droplets separated from each other, the laser source 64 is a pulsed source. To give an order of magnitude, 10,000 droplets can be ejected per second. For example, the laser source 64 is a laser source with a wavelength of 1,064 nm.

In addition to the laser source, the printing device 50 includes an optical system 68 which enables the adjustment of the focus along a Z axis perpendicular to the depositing surface 56. The optical system 68 advantageously includes a lens which makes it possible to focus the laser beam 66 onto an impacted area. The optical system 68 preferably includes a mirror to change the position of the impacted area. The optical system 68 thus makes it possible to change the area impacted by the laser beam in an impact plane referenced Pi in FIG. 3. The laser source 64 and the optical system 68 are not further described either, since they are known to the persons skilled in the art and may be identical with those of the prior art.

The printing device 50 also comprises at least one donor substrate 70 which comprises, according to one embodiment, an absorbent layer 72 for the wavelength of the laser beam 66 whereon a film 74 of at least one bio-ink is affixed. In the following part of the description, film means that the bio-ink occupies a volume with a thickness (the dimension in a direction perpendicular to the plane of impact Pi) of less than 500 µm. Unlike a tank, the fact that bio-ink is packaged as a film can make it possible to avoid settling phenomena.

The absorbent layer 72 is made of a material adapted to the wavelength of the laser beam 66 to transform the light energy into a punctual heating of the absorbent layer 72. The donor substrate 70 is preferably so positioned that the optical system focuses the laser beam at the absorbent layer 72. According to one embodiment, the absorbent layer 72 is made of gold, titanium, or another component according to the wavelength of the laser beam 66. According to another embodiment, the donor substrate 70 includes no absorbent layer 72. In this case, the laser beam 66 energy is absorbed by the ink.

The donor substrate 70 preferably comprises a blade 76 made of a material transparent for the wavelength of the laser beam 66 which includes, on one of its faces, a coating corresponding to the absorbent layer 72. The presence of the blade 76 imparts stiffness to the donor substrate 70 which makes it possible to handle and keep the ink and/or the substantially flat absorbent layer 72 in the impact plane Pi. The bio-ink film 74 comprises a free surface 78 which is spaced from the absorbent layer 72 by a distance E corresponding to the thickness of the film 74 and which is spaced from the depositing surface 56 by a distance L. The free surface 78 and the depositing surface 56 face each other.

As illustrated in FIG. 3, the laser beam 66 is adapted to produce a cavity 80 at the interface between the absorbent layer and the bio-ink film 74 which generates a droplet 82 which detaches from the free surface 78 to move to the depositing surface 56. In the following part of the description, a vertical direction is parallel to the gravitational force G and the up-down direction corresponds to the direction of the gravitational force G. The direction of the laser beam 66 and the direction of the droplet movement are parallel to the vertical direction.

Upward Printing:

According to one characteristic of the invention, the laser beam 66 and thus the movement of the droplet 82 are oriented in the opposite direction relative to the gravitational force G. The free surface 78 of the bio-ink film 74 is thus directed upwards. When moving from the bio-ink film 74 to the depositing surface 56, the droplet 82 moves upwards in the down-up direction.

This configuration provides the following advantages:
  It limits the appearance of settling phenomena, with the bio-ink being in the form of a film,
  It makes it possible to obtain a substantially constant thickness E for the bio-ink film 74, with the influence of the gravitational force G on the shape of the free surface 78 of the film 74 being limited by the free surface 78 being oriented upward, It makes it possible to use a wide range of bio-inks when an independent absorbent layer 72 of the bio-ink film 74 is used to transform the light energy into a punctual heating.

Almost zero kinetic energy at the time of depositing a droplet onto the receiving substrate:

The formation of a droplet 82 from a bio-ink film will depend on many parameters, mainly the characteristics of the bio-ink, the characteristics of the laser beam and the conditions of implementation. FIGS. 4A to 4D show the evolution during the time of deformation of the free surface of the bio-ink film, which results, or not, in the formation of a droplet, for different values of the beam laser 66 energy, with the latter having an energy of 21 µJ in FIG. 4A, 35 µJ in FIG. 4B, 40 µJ in FIG. 4C and 43 µJ in FIG. 4D. For the same bio-ink and under the same embodiment conditions, it can be noted that several rates exist, according to the energy of the laser beam.

Figure 4A:
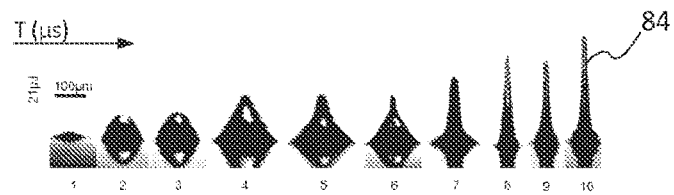
FIGS. 4A to 4D are side views illustrating the formation or not of a droplet according to different rates.

As illustrated in FIG. 4A, if the energy of the laser beam is less than a lower threshold, the droplet does not detach from the bio-ink film 74. Since the maximum height of the deformation 84 generated at the free surface 78 of the ink film 74 is less than the distance L between the film 74 and the depositing surface 56, no element is printed. According to the selected example, the lower threshold ranges from 21 µJ to 35 µJ. As illustrated in FIG. 4D, if the energy of the laser beam is above an upper threshold, the gas bubble 80 produced inside the film breaks at the free surface thus causing the uncontrolled projection of microdroplets. According to the selected example, the upper threshold ranges from 40 µJ to 43 µJ.

Figure 4B:
Figure 4C:
Figure 4D:
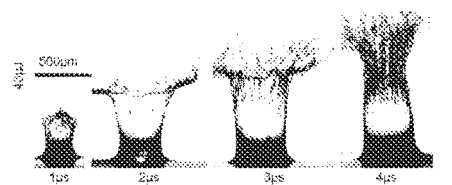

Between the lower and upper thresholds, as illustrated in FIGS. 4B and 4C, the rate is such that it enables the formation of a jet. If the distance L separating the film 74 and the depositing surface 56 is sufficient, this rate enables the formation of a droplet. Preferably, the distance L is of the order of 1 to 2 mm to enable the formation of a droplet and not of a continuous jet which stretches out from the film up to the depositing surface. This configuration limits the risks of contamination of the biological tissue achieved by the bio-ink.

Figures 5A, 5B, 5C, 5D:
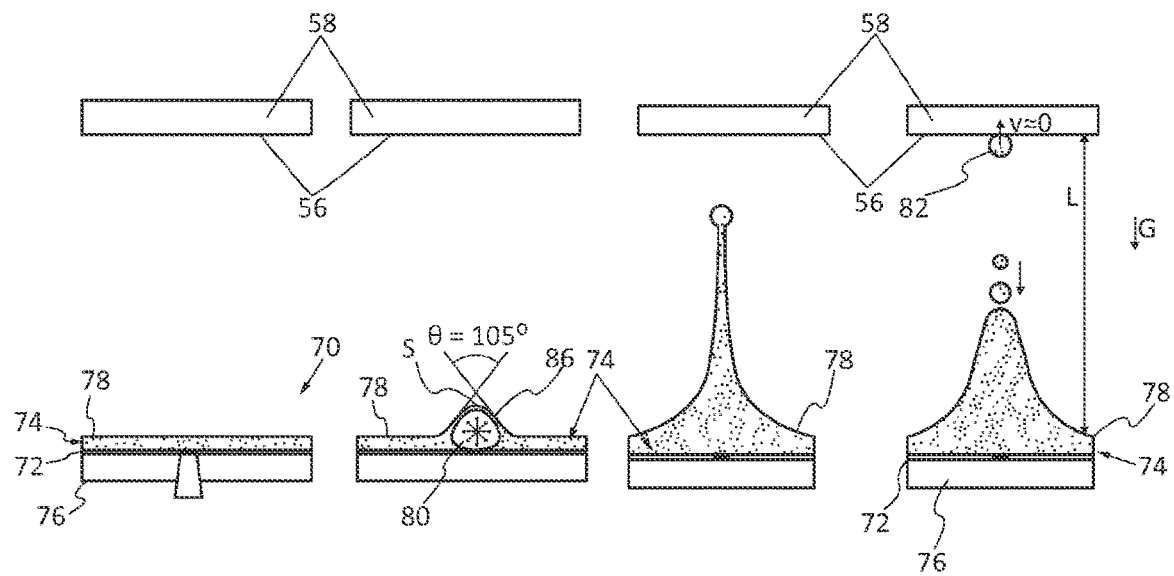
FIGS. 5A to 5D are diagrams illustrating a droplet at different times of its formation, with the last FIG. 5D illustrating the moment when a droplet reaches a receiving substrate.

According to another characteristic of the invention, for the same bio-ink and under the same embodiment conditions, the distance L separating the ink film 74 and the depositing surface 56 and/or the beam laser 66 energy are so adjusted that the kinetic energy of the droplet is almost equal to zero when the droplet 82 contacts the depositing surface 56, as illustrated in FIG. 5D. This configuration limits the risk of damaging the elements to be printed which are cells. Almost equal to zero means that the kinetic energy is null or slightly positive to enable the droplet to settle down on the depositing surface 56. This circumstance is made possible because the droplet 82 moves in the opposite direction relative to the gravitational force G.

The distance L separating the bio-ink film 74 and the depositing surface 56 is preferably stationary. Thus, the laser beam 66 energy is so adjusted that the kinetic energy of the droplet is almost equal to zero when the droplet 82 contacts the depositing surface 56.

Calibration Technique:

As indicated above, the formation of the droplet is not related to the energy of the laser beam only. It is also related to the nature of the bio-ink especially the viscosity, the surface tension and the conditions of implementation thereof. FIGS. 5A to 5D, 7A to 7D illustrate a calibration method for determining the energy of the laser beam for obtaining an optimal rate for the formation and the deposition of droplets, specifically a rate that leads to a deposit at zero speed at a given distance L. FIGS. 5A to 5D show some of the steps of forming a droplet 82 between the time of impact of the laser beam shown in FIG. 5A and the deposition of the droplet 82 on the depositing surface 56. According to one characteristic of the invention, the calibration method for adjusting the laser energy comprises the steps of measuring an included angle θ of a deformation 86 of the free surface 78 of the film 74 of bio-ink at a set time TI after the impact of the laser beam 66 and of adjusting the energy of the laser beam 66 according to the measured value of the included angle θ.

Figure 7A:
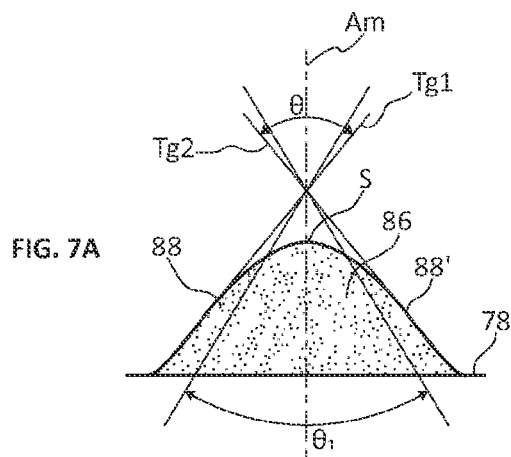
FIGS. 7A and 7B are side views illustrating the formation of a protrusion on the free surface of a bio-ink film prior to the formation of a droplet, produced at the same time but with different energies for the laser beam.
Figure 7B:
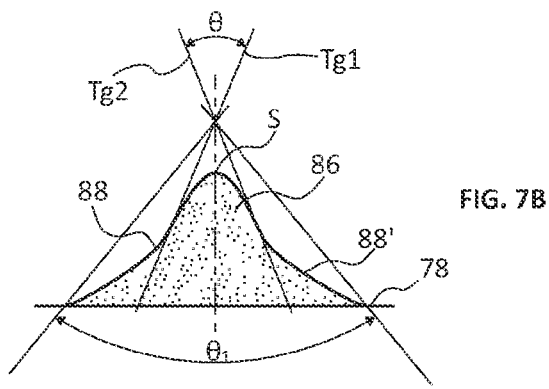
Figure 8:
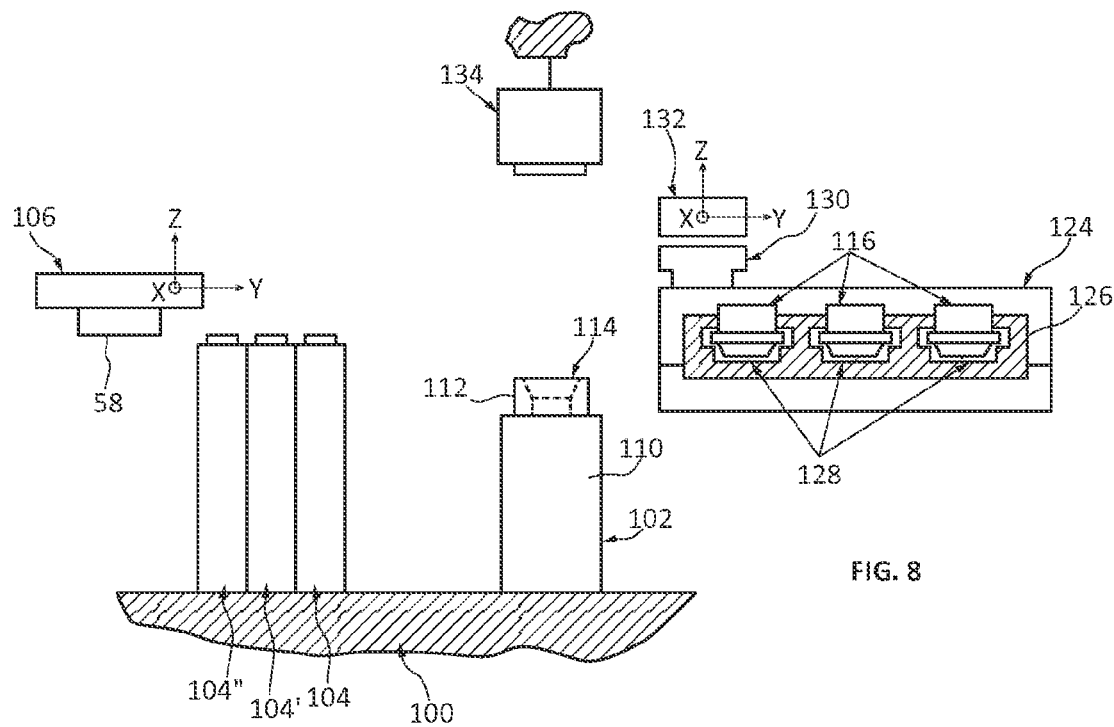
FIG. 8 is a schematic representation of a printing device according to one embodiment of the invention which combines at least one laser-type print head and at least one ink-jet-type print head.
Figure 9:
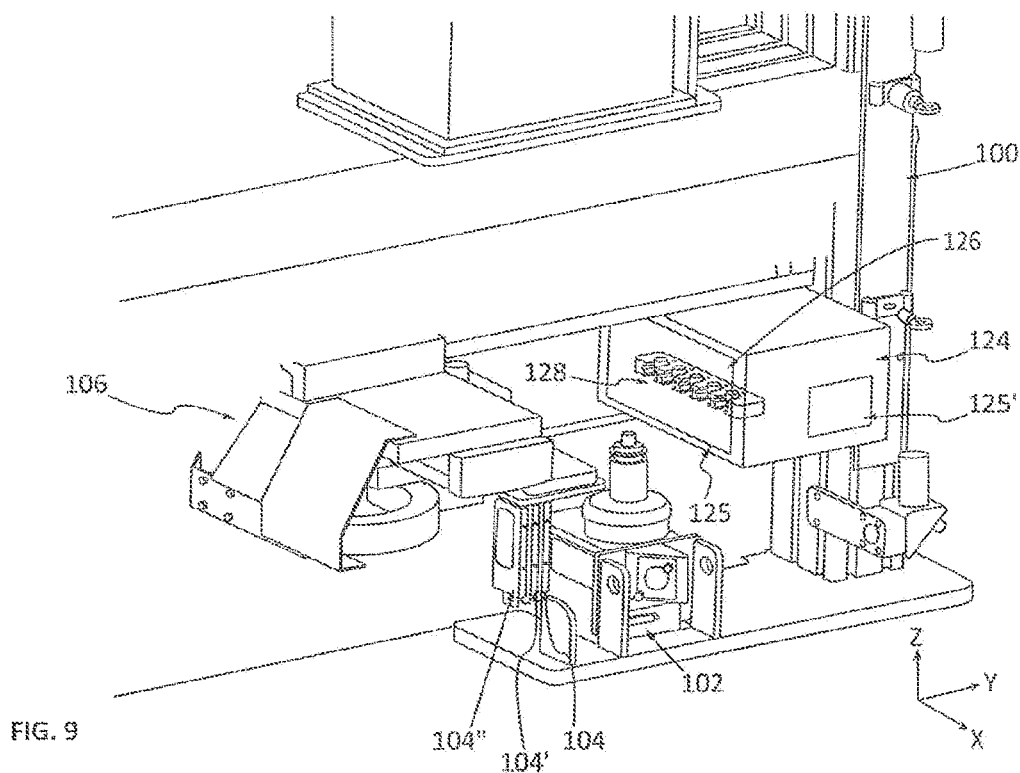
FIG. 9 is a perspective view of a printing device according to one embodiment of the invention which combines a laser-type print head and several ink-jet-type print heads.

As illustrated in FIGS. 5B, 7A and 7B, the deformation 86 has a symmetrical shape with respect to a median axis Am parallel to the vertical direction. This deformation 86 includes a vertex S centered on the center axis Am. This vertex S corresponds to the deformation area 86 furthest from the rest of the free surface 78 of the film 74. In a plane containing the median axis Am, the vertex S is extended by a first flank 88 on one side of the median axis Am and by a second flank 88' on the other side of the median axis Am, with both flanks 88, 88' being symmetrical with respect to the median axis Am.

Each face 88, 88' comprises a point of inflexion. The first flank 88 comprises a first tangent TgI at its inflexion point and the second flank 88 includes a second tangent Tg2 at its inflexion point, with the two tangents TgI and Tg2 being secant at a point of the median axis Am. The included angle θ corresponds to the angle formed by the tangents TgI and Tg2 and facing the film 74 (or downwards).

For the formation of a droplet, the included angle θ must be smaller than or equal to a first threshold θ1. As illustrated in FIG. 7A, if the included angle θ is above the first threshold θ1, the energy of the laser beam is thus not sufficient to generate a droplet. On the contrary, as shown in FIG. 7B, if the included angle θ is smaller than the first threshold θ1, the laser beam energy is sufficient to generate a droplet.

To obtain a near-zero kinetic energy when the formed droplet reaches the depositing surface 56 at a distance L from the free surface 78 of the film 74, the included angle θ must be greater than or equal to a second threshold θ2. The value of the included angle θ is preferably determined using a take at the time TI of the deformation 86. In one embodiment, the take is performed using a camera, the axis of sight of which is perpendicular to the vertical direction.

The time TI depends on the film thickness and very little varies from one ink to another. The time TI is advantageously of the order of 4 to 5 µs from the impact of the laser beam for a thickness E of the film of the order of 40 to 50 µm. This time TI is illustrated in FIG. 5B. The first threshold θ1 is approximately equal to 105°. Thus, if at the time TI the included angle θ is less than or equal to 105°, the laser beam energy is sufficient to generate a droplet 82.

The second threshold θ2 depends on the distance L between the depositing surface 56 and the free surface 78 of the ink film 74. The second threshold θ2 is inversely proportional to the distance L. The second threshold θ2 is high and equal to approximately 80° for a small distance L, of the order of 1 mm. A relatively small distance L will be preferred to reduce the stresses in the jet and at the time of the contact of the droplets with the depositing surface. The second threshold θ2 is low and equal to approximately 50° for a substantial distance L of the order of 10 mm. A relatively long distance L will be preferred if a remote printing is desired, for instance, if the donor substrate 70 has larger dimensions than those of the well at the bottom of which the depositing surface 56 is positioned. This technique for calibrating the laser beam energy makes it possible to optimize the speed of the jet by reducing it in order to limit the risks of damaging the elements contained in the ink particularly at the time of deposition on the depositing surface 56.

Thickness of the Ink Film:

The bio-ink composition preferably includes a high concentration in elements to be printed 62 in order to obtain a biological tissue with a high concentration in cells. In this case, as illustrated in FIG. 3, the droplet 82 includes a volume fraction with a high concentration in elements to be printed 62.

For bio-inks with a high concentration, the thickness E of the film 74 is of the order of 40 to 60 μm. In order to improve the accuracy of the deposition of the elements to be printed, the film 74 of bio-ink advantageously has a thickness E ranging from 1.5D to 2D, with D being the diameter of the elements to be printed 62 which have an approximately spherical shape or the diameter of a sphere wherein an element to be printed 62 is inscribed. According to one embodiment, the film 74 of bio-ink has a thickness E greater than or equal to 20 μm for smaller elements to be printed which have a diameter of the order of 10 to 15 μm. The thickness E of the film may be of the order of 400 μm when elements to be printed 62 are cell aggregates. Generally, the thickness E of the film is less than 100 μm when the elements to be printed 62 are unit cells.

Preferably, the film 74 is characterized by a (dimension of the free surface 78)/(film thickness 74) ratio greater than or equal to 10, and advantageously greater than or equal to 20. The size of the free surface 78 corresponds to the largest dimension of the free surface 78 of the film 74 in a plane parallel to the plane of impact Pi.

Printing Technique Combining a Laser-Type Print Head and a Nozzle Print Head:

According to another characteristic of the invention, the printing method uses at least one laser-type print head for at least a first bio-ink and at least one nozzle print head for at least a second bio-ink. This combination makes it possible to increase the production rate.

Figure 1:
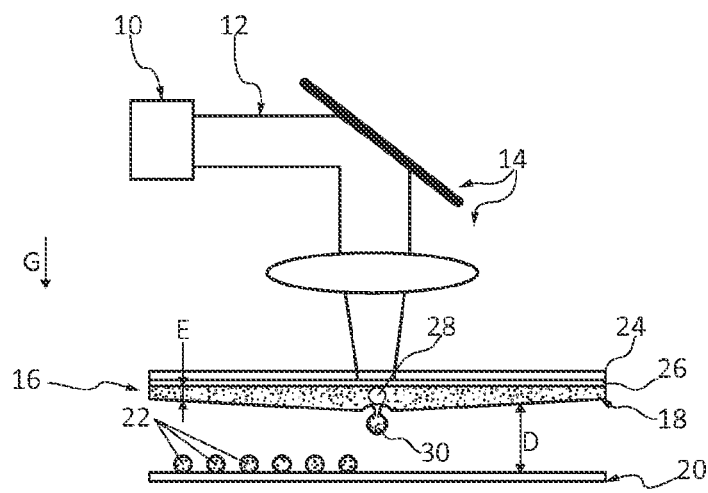
FIG. 1 is a schematic representation of a laser printing device which illustrates an alternative solution of the prior art.
Figure 2:
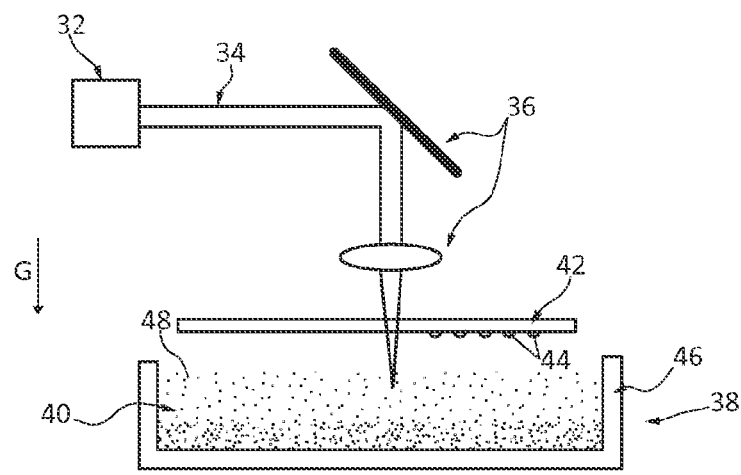
FIG. 2 is a schematic representation of a laser printing device which illustrates another alternative solution of the invention.

Nozzle print head means a print head which comprises an orifice through which the second bio-ink passes. Thus, a nozzle print head may be a print head of the ink-jet type, a microvalves print head, a print head of the bio-extrusion type. Each print head of the laser type is preferably the same as the one described in FIG. 3. However, the invention is not limited to this type of laser print head. Using laser-type print heads as described in FIGS. 1 and 2 or other print heads can be considered. The nozzle print heads are not described any further since they are preferably identical with those of the prior art.

In the case of a biological tissue comprising disjoint cells separated by extracellular materials, the extracellular materials are preferably deposited by the nozzle print head (s) and the cells are preferably deposited by the laser-type print head(s). As the extracellular materials are less sensitive to shear effects, they can be deposited using a nozzle print head. As the bio-ink cartridges intended for the nozzle print heads have a very much higher volume than the volume of ink (of the order of 40 μm) supported by a donor substrate 70 intended for a laser-type print head, the materials of the extracellular matrix can be deposited with a high flow rate. Although a nozzle print head is capable of depositing inks with a high flow rate, as each donor substrate intended for a laser type print head supports a very small volume of ink, it is necessary to change these frequently, which tends to increase the removal time relative to a nozzle print head.

According to another characteristic, the laser type print head(s) and the nozzle print head(s) are integrated in the same machine and move in the same coordinate system. This configuration makes it possible to simplify the relative positioning of the various print heads, to improve the accuracy of the removal and to guarantee the integrity of the printed elements.

Printing Device Comprising a Donor Substrates Storage Chamber:

FIGS. 8 to 11 show a printing device according to one embodiment of the invention. The printing device 100 includes a chassis supporting a print head 102 of the laser type and several print heads 104, 104', 104" of the ink-jet type. The chassis 100 includes a coordinate system X, Y, Z, with the Z axis being oriented in the vertical direction, and with the X, Y plane corresponding to a horizontal plane.

The print heads 102, 104, 104', 104" are stationary with respect to the chassis 100 and positioned so that the droplets are emitted vertically upwards. The print heads 102, 104, 104', 104" are offset in a first direction parallel to the Y axis. In one embodiment, the print heads 104, 104', 104" of the ink-jet type are joined together. The print head 102 of the laser type is spaced from the print heads 104, 104', 104" of the ink-jet type.

Figure 10:
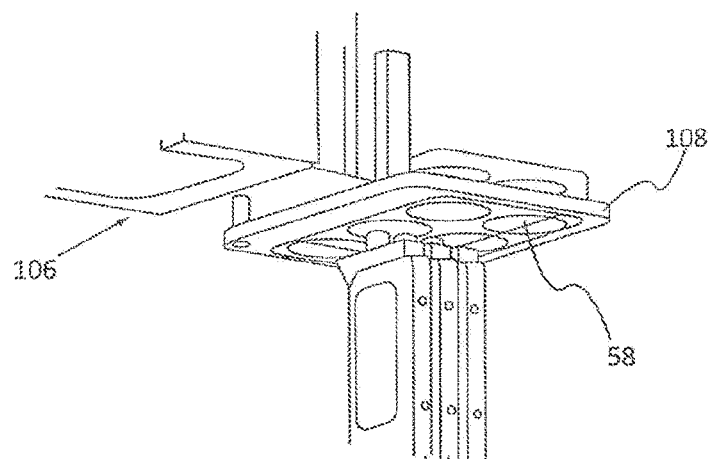
FIG. 10 is a perspective view of a part of the printing device of FIG. 9 when printing with an ink-jet-type print head.

The printing device also comprises a mobile chassis 106, a system for guiding and moving the mobile chassis 106 relative to the chassis 100 in three directions parallel to the X, Y, Z axes and a control system for controlling the displacements of the mobile chassis 106. The guide and displacement system and the control system are so selected as to achieve a micrometric precision as regards the movements of the mobile chassis 106 relative to the chassis. As illustrated in FIG. 10, the mobile chassis 106 includes a frame 108 for releasably attaching at least one receiving substrate 58. When it is secured to the mobile frame, the movements of the receiving substrate 58 are controlled with micrometric precision.

The print head 102 of the laser type comprises a hollow cylindrical body 110, stationary relative to the chassis, which contains a part of an optical system and whereon a tubular portion 112 is positioned which includes an upper end 114 which opens into a horizontal plane. These elements are so configured that a laser beam guided by the optical system scans the section of the upper end 114. Each donor substrate 70 has the shape of a disk positioned on a base 116.

Figure 11:
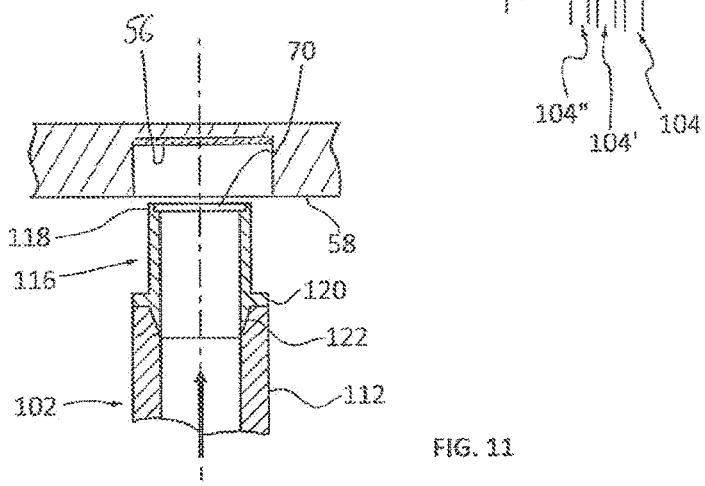
FIG. 11 is a sectional view of a part of the printing device of FIG. 9 when printing with an laser-type print head.

According to one embodiment illustrated in FIG. 11, each base 116 has the shape of a tube which comprises, at its upper edge, a recess 118 which has a diameter identical to that of a donor substrate 70 and a height sufficient to hold same. This recess 118 thus makes it possible to position a donor substrate 70 relative to the base which supports same.

The upper end 114 and the base 116 have shapes that cooperate with each other so that the base 116 is immobilized in a given position relative to the upper end 114 and thus with respect to the X, Y, Z system of the chassis. According to one embodiment, the base 116 includes an outer flange 120 which bears against the upper end 114 and makes it possible to position the base along the Z axis. Under the base plate 120, the base 116 includes a frustoconical surface 122 which cooperates with a tapered portion provided inside the tubular portion 112. These shapes make it possible to center the base 116 relative to the tubular portion 112 and to position same in an XY plane. Magnetic materials can preferably be used to improve the positioning of the base 116 relative to the tubular portion 112.

The printing device 124 advantageously comprises a chamber so configured as to store at least one base 116. The chamber 124 comprises at least one opening 125 for inputting and outputting the stored bases 116. According to one embodiment, the chamber 124 has a parallelepiped shape.

The chamber 124 preferably has dimensions adapted to store several bases. The printing device can thus successively print several bio-inks with the same print head 102 of the laser type.

The bases 116 are stored on a base plate 126 which comprises recesses 128, i.e. one recess for each base 116. The base plate 126 has an elongated shape and comprises, on its whole length, U-shaped notches 128. According to a first alternative solution illustrated in FIG. 8, the length of the base plate 126 is oriented along the Y axis.

According to a second preferred embodiment, the length of the base plate 126 is oriented along the X axis and the notches 128 are open towards the print heads. The chamber 124 advantageously includes, on a first side facing the print heads, a first opening 125 enabling the bases 116 to come out and, on another side, a second opening 125' for introducing the bases 116.

According to one embodiment, the chamber 124 includes a guide system for positioning the base plate 126, for example a rail, with the base plate 126 comprising, in the lower part, a groove the cross-section of which engages with that of the rail. This rail opens at the second opening 125'. It is preferably oriented along the X axis.

The chamber 124 comprises containment means for preserving, inside the chamber, an atmosphere adapted to bio-inks, in particular as regards temperature and/or hygrometry. Such containment means are provided in particular at each opening 125, 125'. They may take the form of a barrier or an air curtain.

In addition to the chamber, the printing device includes a mobile clamp 130 to move the bases between the chamber 124 and the print head 102 of the laser type. In a first alternative solution, the mobile clamp 130 is secured to a mobile carriage 132, independent of the mobile frame 106, which is configured to move in the X, Y, Z directions. According to another alternative solution, the mobile clamp 130 is secured to the mobile frame 106.

According to one embodiment, the printing device includes a shooting device (not shown), the line of sight of which is perpendicular to the vertical direction and faces the upper surface of the donor substrate. This device can be used to calibrate the energy of the laser beam of the print head 102 of the laser type.

Figure 12:
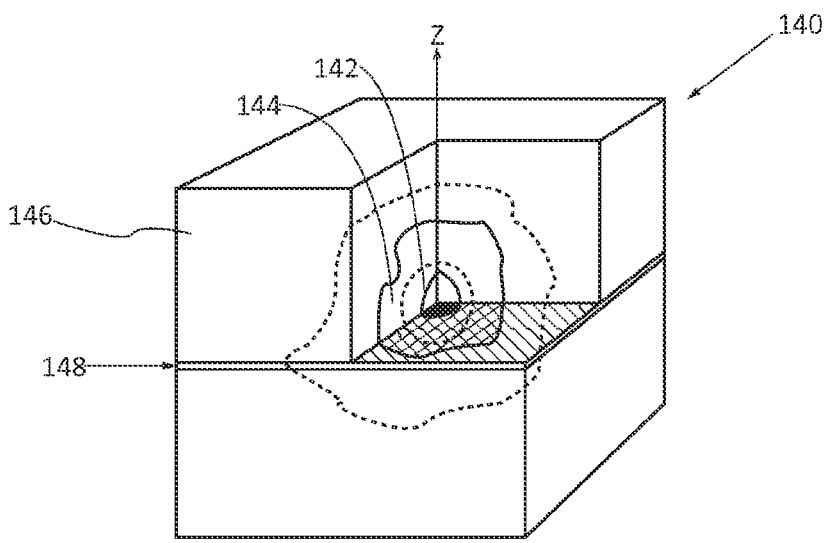
FIG. 12 is a perspective view of a 3-dimensional representation of a portion of a biological tissue which is to be replicated.

Method for Producing a Biological Tissue Using Bio-Printing:

The first step of said method consists in generating a three-dimensional digital representation of the biological tissue to be printed. In FIG. 12, a portion of such a representation as a cube is shown (140) which has a first volume region 142 positioned inside within a second volume region 144 itself positioned in a third volume region 146. For the purpose of the description, the representation 140 is greatly simplified.

Each volume region 142, 144, 146 is colored or textured differently, with each color or texture corresponding to a set of characteristics among the following (not limited) ones: material, manufacturing means, trajectory, . . . . Each color or texture preferably corresponds to a bio-ink. All the volume regions 142, 144 and 146 are closed. The representation advantageously comprises a plurality of small elementary volume which have different colors or textures depending on the volume region which they belong to. According to one embodiment, the representation 140 originates from a computer file of the PLY type.

Figure 13:
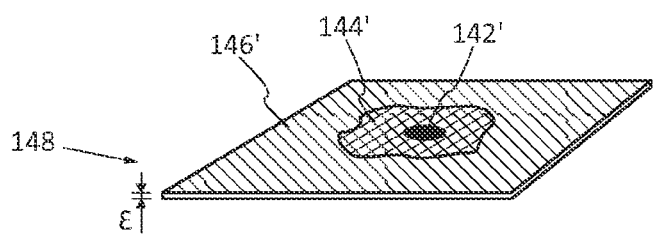
FIG. 13 is a perspective view of a slice of the representation of FIG. 12.

The second step of the method consists in slicing the representation 140 into a succession of stacked layers along an axis Z. In FIG. 13, a layer 148 of the 140 representation has been separated. When slicing the representation 140, in line with a change of volume region, each layer comprises an edge which corresponds to a new region.

As illustrated in FIG. 13, the layer 148 comprises a first region 142' which corresponds to the first volume region 142, a second region 144' which corresponds to the second volume region 144 and a third region 146' which corresponds to the third volume region 146. For each layer, the regions 142', 144', 146' are colored or textured according to the color or texture of the volume regions 142, 144, 146. Each layer has a thickness £ which is determined according to the height of the printed droplets. If the layer comprises only one material to be printed, the layer has a thickness substantially equal to the height of a droplet.

When the layer comprises several materials to be printed, in a first alternative solution, the layer has a thickness equal to the lowest common multiple of the heights of the droplets associated with each material. This alternative solution has the advantage of minimizing any shifting on the whole height of the object to be printed and to achieve fast printing. According to a second alternative solution, the layer has a thickness equal to the highest common factor of the heights of the droplets associated with each material. This alternative solution has the advantage of increasing the resolution and the number of layers.

For example, if the first material is printed using laser bio-printing, the printed droplets have a height of the order of 10 µm. If the second material is printed using microvalves bio-printing, the printed droplets have a height of the order of 100 µm. In the first alternative solution, the layers have a thickness of the order of 100 µm. In the second alternative solution, the layers have a thickness of the order of 10 µm.

Preferably, each layer comprises a plurality of small elementary, for example triangular, polygons which have different colors according to the region which they belong to. The object to be printed thus corresponds to a set of layers which each comprise a set of polygons, each having an associated color or texture.

Figure 14:
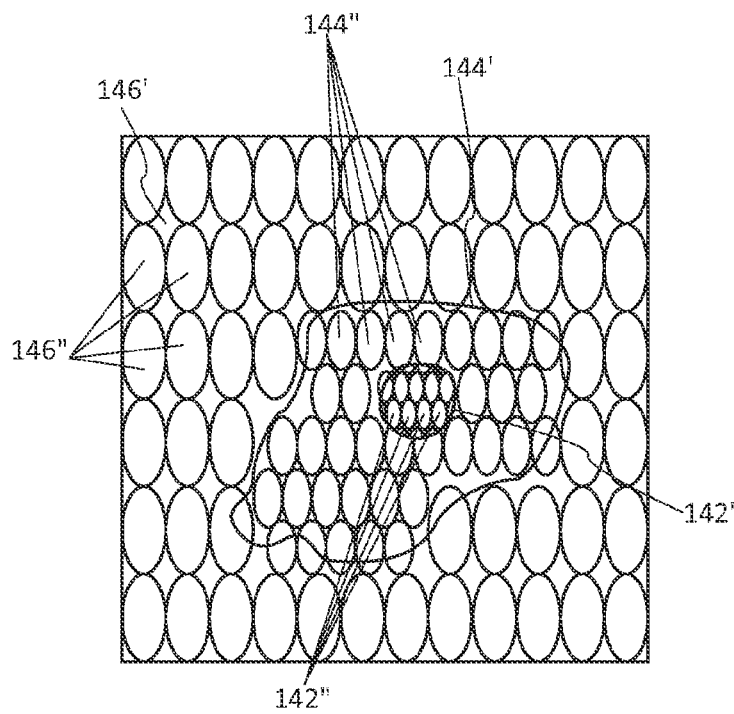
FIG. 14 is a top view of the slice of FIG. 13 illustrating the positioning of the bio-inks droplets.

A third step of the method consists in determining, for each layer, the position of the droplets to be printed of each bio-ink according to the colored or textured regions 142', 144', 146' and the expected volume of each droplet. For this purpose, each region 142', 144', 146' of each layer is filled with ellipses 142", 144", 146", the dimensions of which depend on the dimensions of the droplets of the bio-ink to be printed in said region, as shown in FIG. 14. For each region, the ellipses have the same dimensions. All the ellipses have parallel focal axes.

The elliptical shape makes it possible to adjust the distances between the droplets in two directions (a first direction parallel to the focal axes and a second direction perpendicular to the first one). The center of each ellipse corresponds to the position of the center of a droplet. The ellipses are positioned region by region, in the descending order of sizes, thus the larger ellipses arranged in the region 146' are positioned first and the smaller ellipses arranged in the region 142' are positioned last.

Preferably at a region change, the positioning is optimized according to two criteria:

the maximum ratio of elementary polygons having the right color or texture in an ellipse, of the order of 75% for example, the minimum ratio of elementary polygons having the wrong color or texture in an ellipse, of the order of 5% for example.

Ellipses Overlapping can be Tolerated.

A fourth step of the method consists in synchronizing the movement of the depositing surface 56 whereon the bio-ink droplets are printed and the various print heads. For bio-laser printing, the laser focusing area is the center of each laser printed ellipse, and each ellipse is the subject of a laser pulse. In this case, the depositing surface is stationary, the laser scans the entire depositing surface. For a depositing surface larger than the donor substrate, the substrate can also be moved (where the depositing surfaces are tipped on) in synchronization with the laser scan.

For a nozzle bio-printing, the center of each ellipse corresponds to the assumed point of impact of a droplet on the depositing surface 56. In this case, the print nozzle is stationary, the substrate moves. However, the print nozzle may be movable.

Applications:

Bio-printing according to the invention can be used to produce:

Implantable tissues for regenerative medicine,

Individualized tissues, made from the patient's cells, making it possible to select in vitro treatments and to develop personalized therapeutic solutions, Predictive models reproducing the physiology of sound human tissues or tissues affected by a pathology in order to predictively test the efficacy or the toxicity of the molecules, of ingredients and of the drug candidates.

By way of example and without limitation, the biological tissue is a bone tissue.

What is claimed is:

1. A printing system comprising:
   (a) a receiving substrate including a depositing surface;
   (b) at least one bio-ink including cells and an extracellular matrix;
   (c) at least one laser print head configured to deposit at least one droplet of the at least one bio-ink onto the depositing surface of the receiving substrate;
   (d) at least one nozzle print head configured to deposit at least one droplet of the at least one bio-ink onto the depositing surface of the receiving substrate;
   (e) the laser print head and the nozzle print head being integrated in a same machine and being moveable in a same coordinate system; and
   (f) laser beam-induced heat operably creating a bubble and upwardly moving the at least one bio-ink from a bio-ink film to the receiving substrate.

2. The printing system according to claim 1, further comprising a biological tissue comprising the cells and the extracellular matrix, the extracellular matrix being deposited by the at least one nozzle print head and the cells being deposited by the at least one laser print head.

3. The printing system according to claim 1, further comprising a controller configured to:
   generate a three-dimensional digital representation of a biological tissue to be produced, with the representation comprising several colored or textured volume regions, with each color or texture being associated with the at least one bio-ink;
   slice the representation into a succession of stacked layers, with each layer comprising the colored or textured regions;
   determine, for each layer, a position of droplets to be printed of the at least one bio-ink according to the colored or textured regions and an expected volume of each droplet; and
   print different droplets using the at least one laser print head and the at least one nozzle print head moving in the same coordinate system.

4. The printing system according to claim 1, further comprising:
   a chamber configured to store at least a base supporting a donor substrate, with the chamber internally maintaining an atmosphere adapted to store the at least one bio-ink;
   a movable clamp for moving bases between the chamber and the laser print head; and
   a mobile chassis supporting the receiving substrate, and multiples of the at least one bio-ink with different characteristics being emitted from the at least one print head.

5. The printing system according to claim 1, further comprising:
   a mobile chassis configured to support the receiving substrate; and
   a controller configured to control movements of the mobile chassis.

6. The printing system according to claim 1, further comprising a laser beam being pulsed and the at least one bio-ink droplet being generated on each laser beam pulse, and the at least one bio-ink comprising an aqueous medium.

7. The printing system according to claim 1, further comprising a laser being configured to emit a pulsed laser beam, a lens configured to focus the pulsed laser beam on an axis perpendicular to the depositing surface, and the laser print head being operable to eject 10,000 droplets of the at least one bio-ink per second.

8. The printing system according to claim 1, wherein the at least one bio-ink is a film with a thickness less than 500 μm, further comprising a donor substrate including an absorbent layer adapted to a wavelength of a laser beam to transform light energy thereof into heating of the absorbent layer.

9. The printing system according to claim 1, further comprising a laser beam focused 40-80 μm below a surface of the at least one bio-ink, and the at least one bio-ink droplet being emitted from the surface toward the receiving substrate in a direction opposite gravity.

10. A printing system comprising:
    (a) at least one receiving substrate with a depositing surface;
    (b) at least one laser print head;
    (c) at least one pulse laser source configured to emit a laser beam;
    (d) optics operably focusing and orienting the laser beam;
    (e) at least one donor substrate which comprises at least one bio-ink;
    (f) at least one nozzle print head operably printing at least one bio-ink on the same receiving substrate as the at least one laser print head;
    (g) a laser beam being pulsed and a bio-ink droplet being generated on each laser beam pulse, and
    (h) the bio-ink droplet being emitted from the depositing surface toward the at least one receiving substrate in a direction opposite gravity.

11. The printing system according to claim 10, further comprising a biological tissue comprising cells and an extracellular matrix, the extracellular matrix being deposited by the at least one nozzle print head and the cells being deposited by the at least one laser print head.

12. The printing system according to claim 10, further comprising:
- a mobile chassis configured to support the at least one receiving substrate; and
- a controller configured to control movements of the mobile chassis.

13. The printing system according to claim 10, further comprising:
- a movable clamp for moving bases between a chamber and the at least one laser print head;
- a mobile chassis supporting the at least one receiving substrate, a guide operably moving the mobile chassis in three directions, a controller configured to control movements of the mobile chassis, and the guide and the controller having a micrometric precision; and
- a mobile clamp secured to the mobile chassis.

14. A printing system comprising:
- (a) at least one receiving substrate with a depositing surface;
- (b) at least one laser print head;
- (c) at least one pulse laser source configured to emit a laser beam;
- (d) optics operably focusing and orienting the laser beam;
- (e) at least one donor substrate which comprises at least one bio-ink;
- (f) at least one nozzle print head operably printing at least one bio-ink on the same receiving substrate as the at least one laser print head;
- a chamber configured to store at least one base supporting a donor substrate, with the chamber being equipped with containment means making it possible to maintain inside an atmosphere adapted to the at least one bio-ink;
- the chamber being adapted to store several of the bases and at least one base plate which comprises recesses, with the base plate being configured as to be stored inside the chamber;
- the at least one base plate comprising a guide for positioning same in the chamber; and
- the chamber comprising, on a first side facing the at least one laser print head, a first opening configured to output bases and, on another side, a second opening configured to introduce the bases.

15. The printing system according to claim 14, further comprising a laser beam being pulsed and a bio-ink droplet being generated on each laser beam pulse, and the bio-ink droplet being emitted from the depositing surface toward the at least one receiving substrate in a direction opposite gravity.

16. A printing system comprising:
- (a) a receiving substrate;
- (b) at least one bio-ink including cells and an extracellular matrix;
- (c) at least one laser print head configured to deposit at least one droplet of the at least one bio-ink onto the receiving substrate;
- (d) at least one nozzle print head configured to deposit at least one droplet of the at least one bio-ink onto the receiving substrate;
- (e) the laser print head and the nozzle print head being moveable along a common coordinate system;
- (f) a laser source configured to emit a laser beam;
- (g) optics configured to focus and orient the laser beam; and
- (h) a blade stiffening a donor substrate and causing the at least one bio-ink to be on an impact plane of the laser beam, and the blade including a material transparent for a wavelength of the laser beam.

17. The printing system according to claim 16, further comprising a bubble is created due to laser beam-induced heat, and the at least one bio-ink is upwardly moved from a bio-ink film to the receiving substrate.

18. The printing system according to claim 16, further comprising:
- a chamber configured to store a base supporting a donor substrate, with the chamber internally maintaining an atmosphere adapted to store the at least one bio-ink;
- multiples of the at least one bio-ink having different characteristics and being emitted from the at least one print head;
- a movable clamp for moving bases between a chamber and the laser print head;
- a mobile chassis supporting the receiving substrate; and
- the laser beam being pulsed.

19. The printing system according to claim 16, further comprising:
- a mobile chassis configured to support the at least one receiving substrate; and
- a controller configured to control movements of the mobile chassis.

20. The printing system according to claim 16, further comprising a biological tissue comprising the cells and the extracellular matrix, the extracellular matrix being deposited by the at least one nozzle print head and the cells being deposited by the at least one laser print head.

* * * * *